United States Patent
Hlopick et al.

(10) Patent No.: US 12,064,559 B2
(45) Date of Patent: Aug. 20, 2024

(54) SEALING ARRANGEMENT FOR FORMING A SEAL BETWEEN A PATIENT AND A PATIENT INTERFACE DEVICE

(71) Applicant: KONINKLIJKE PHILIPS N.V., Eindhoven (NL)

(72) Inventors: Stephen George Hlopick, Murrysville, PA (US); Lauren Patricia Chodkowski, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 216 days.

(21) Appl. No.: 17/335,556

(22) Filed: Jun. 1, 2021

(65) Prior Publication Data

US 2021/0379311 A1  Dec. 9, 2021

Related U.S. Application Data (60) Provisional application No. 63/036,067, filed on Jun. 8, 2020.

(51) Int. Cl.
*A61M 16/06* (2006.01)

(52) U.S. Cl.
CPC .... *A61M 16/0622* (2014.02); *A61M 16/0633* (2014.02); *A61M 16/0688* (2014.02)

(58) Field of Classification Search
CPC ............ A61M 16/06–0694; A61M 2016/0661
See application file for complete search history.

(56) References Cited

U.S. PATENT DOCUMENTS

| | | | |
|---|---|---|---|
| 3,357,426 A | 12/1967 | Cohen | |
| 6,196,223 B1 * | 3/2001 | Belfer | A61M 16/0616 128/206.25 |
| 6,341,606 B1 | 1/2002 | Bordewick | |
| 8,302,607 B2 | 11/2012 | Pierce | |
| 8,596,274 B2 | 12/2013 | Hieber | |
| 2002/0185134 A1 | 12/2002 | Bishop | |
| 2005/0284479 A1 | 12/2005 | Hansmann | |

(Continued)

FOREIGN PATENT DOCUMENTS

| | | |
|---|---|---|
| JP | 2006326129 A | 12/2006 |
| WO | 9925410 A1 | 5/1999 |

OTHER PUBLICATIONS

International Search Report for PCT/EP2021/064896 filed Jun. 3, 2021.

*Primary Examiner* — Valerie L Woodward
(74) *Attorney, Agent, or Firm* — Michael W. Haas (57) ABSTRACT

A sealing arrangement for forming a seal between a patient's face and a patient interface device for use in delivering a flow of a treatment gas to the patient includes a generally planar substrate body having a first side and an opposite second side. The substrate body includes a main portion having an opening defined therethrough that is sized and configured to encompass the mouth and nose of the patient. The sealing arrangement further includes a first adhesive layer disposed on the first side of the substrate body and a second adhesive layer disposed on the second side of the substrate body. The first adhesive layer is sized and configured to adhere to the skin of the patient with a first adherence force and the second adhesive layer is sized and configured to adhere to a cushion of the patient interface device with a lesser second adherence force.

13 Claims, 6 Drawing Sheets

(56) References Cited

U.S. PATENT DOCUMENTS

| | | |
|---|---|---|
| 2007/0050883 A1 | 3/2007 | Matich |
| 2008/0302365 A1* | 12/2008 | Cohen ............... A61M 16/0616 128/201.24 |
| 2010/0229872 A1* | 9/2010 | Ho .................... A61M 16/0633 128/206.25 |
| 2011/0005524 A1* | 1/2011 | Veliss ............... A61M 16/0683 128/206.24 |
| 2011/0209701 A1 | 9/2011 | Derringer |
| 2012/0055488 A1 | 3/2012 | Kendall |
| 2012/0204881 A1 | 8/2012 | Davidson |
| 2015/0217071 A1* | 8/2015 | Chodkowski ..... A61M 16/0605 128/206.25 |
| 2016/0114119 A1 | 4/2016 | Bugamelli |
| 2018/0043124 A1 | 2/2018 | Ronayne |
| 2019/0240441 A1* | 8/2019 | Dumas De La Roque ................. A61M 16/0616 |
| 2020/0114109 A1 | 4/2020 | Assi |

\* cited by examiner

SEALING ARRANGEMENT FOR FORMING A SEAL BETWEEN A PATIENT AND A PATIENT INTERFACE DEVICE

CROSS-REFERENCE TO RELATED APPLICATIONS

This patent application claims the priority benefit under 35 U.S.C. § 119(e) of U.S. Provisional Application No. 63/036,067, filed on Jun. 8, 2020, the contents of which are herein incorporated by reference.

BACKGROUND OF THE INVENTION

1. Field of the Invention

The present invention relates to non-invasive ventilation and pressure support systems wherein a patient interface device is used to deliver a flow of breathing gas to a patient and, more particularly, to a sealing arrangement for forming a seal between a patient and a patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, such as obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Recently, PAP machines have also been utilized in treating patients suffering from certain diseases that adversely affect the patient's lungs such as Coronavirus (COVID-19). However, gases expelled from such patients (e.g., via exhaling, coughing, sneezing) may be contaminated with the virus and thus can lead to infections to caregivers and others near the patient.

Non-invasive ventilation and pressure support therapies as just described involve a gas flow generator to produce a flow of breathing gas, and the placement of a patient interface device including a mask component on the face of a patient. The gas flow generator produces positive air pressure by taking air in from the surroundings and spinning a fan to push the air out of the machine, through a delivery conduit, and into the patient interface device to be delivered to the patient. Leak at the patient interface is a known issue for Non-Invasive Ventilation (NIV) Masks. Caregivers are currently instructed to allow some leak to reduce the risk of skin breakdown at the nose bridge. The masks are also known to generally leak. With the incidence of COVID-19, NIV masks put the caregivers and other patients at risk for infection.

SUMMARY OF THE INVENTION

Embodiments of the present invention address shortcomings of conventional arrangements by generally providing a reusable leak-resistant or leak-proof seal at the interface between the patient and the patient interface device while allowing for a looser fit of the patient interface device on the face of the patient than conventional arrangements. As one aspect of the present invention a sealing arrangement for use in forming a seal between a face of a patient and a patient interface device for use in delivering a flow of a treatment gas to the patient is provided. The sealing arrangement comprises: a generally planar substrate body having a first side and a second side opposite the first side, the substrate body comprising a main portion having an opening defined therethrough, the opening being sized and configured to encompass the mouth and nose of the patient; a first adhesive layer disposed on the first side of the substrate body; and a second adhesive layer disposed on the second side of the substrate body, wherein the first adhesive layer is sized and configured to adhere to the skin of the patient adjacent the nose and mouth of the patient with a first adherence force, and wherein the second adhesive layer is sized and configured to adhere to a cushion of the patient interface device with a second adherence force less than the first adherence force.

The substrate body may further comprise an extension tab extending from the main portion and including a portion of the first adhesive layer thereon.

The extension tab may be sized and configured to extend downward along a first side of the mouth of the patient, across below the mouth of the patient, and upward along a second side of the mouth of the patient opposite the first side of the mouth when the sealing arrangement is positioned on the face of the patient with the opening encompassing the mouth and nose of the patient.

The substrate body may further comprise an alignment portion extending from the main portion.

The alignment portion may be delineated from the main portion by a separation feature.

The separation feature may comprise a locally thinned region extending between the alignment portion and the main portion in the substrate body.

The separation feature may comprise a plurality of separations defined through the substrate body.

The alignment portion may be sized and configured to engage a forehead support of the patient interface device.

The substrate body may further comprise an alignment portion extending from the main portion.

The alignment portion may be delineated from the main portion by a separation feature.

As another aspect of the present invention an arrangement for use in delivering a flow of a treatment gas to the patient is provided. The arrangement comprises: a patient interface device having a cushion structured to sealingly engage about the mouth and nose of the patient; and a sealing arrangement comprising: a generally planar substrate body having a first side and a second side opposite the first side, the substrate body comprising a main portion having an opening defined therethrough, the opening being sized and configured to encompass the mouth and nose of the patient; a first adhesive layer disposed on the first side of the substrate body; and a second adhesive layer disposed on the second side of the substrate body, wherein the first adhesive layer is sized and configured to adhere to the skin of the patient adjacent the nose and mouth of the patient with a first adherence force, and wherein the second adhesive layer is adhered to the cushion of the patient interface device with a second adherence force less than the first adherence force.

The opening defined through the main portion of the substrate body may be larger than a corresponding patient opening of the cushion.

As yet another aspect of the present invention, a method of selectively sealing a cushion of a patient interface device to the face of a patient using a sealing arrangement such as previously described is provided. The method comprises: coupling the substrate body of the sealing arrangement to the cushion with the second adhesive layer; coupling the substrate body and the cushion coupled to the substrate body to the face of the patient with the first adhesive layer; uncoupling the cushion from the substrate body while leaving the substrate body coupled to the face of the patient by separating the cushion from the first adhesive layer; and recoupling the cushion to the substrate body while the substrate body is coupled to the face of the patient via the first adhesive layer by re-adhering the second layer of the adhesive to the cushion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled directly in contact with each other (i.e., touching). As used herein, "fixedly coupled" or "fixed" means that two components are coupled so as to move as one while maintaining a constant orientation relative to each other.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality). Directional phrases used herein, such as, for example and without limitation, left, right, upper, lower, front, back, on top of, and derivatives thereof, relate to the orientation of the elements shown in the drawings and are not limiting upon the claims unless expressly recited therein.

Figure 1:
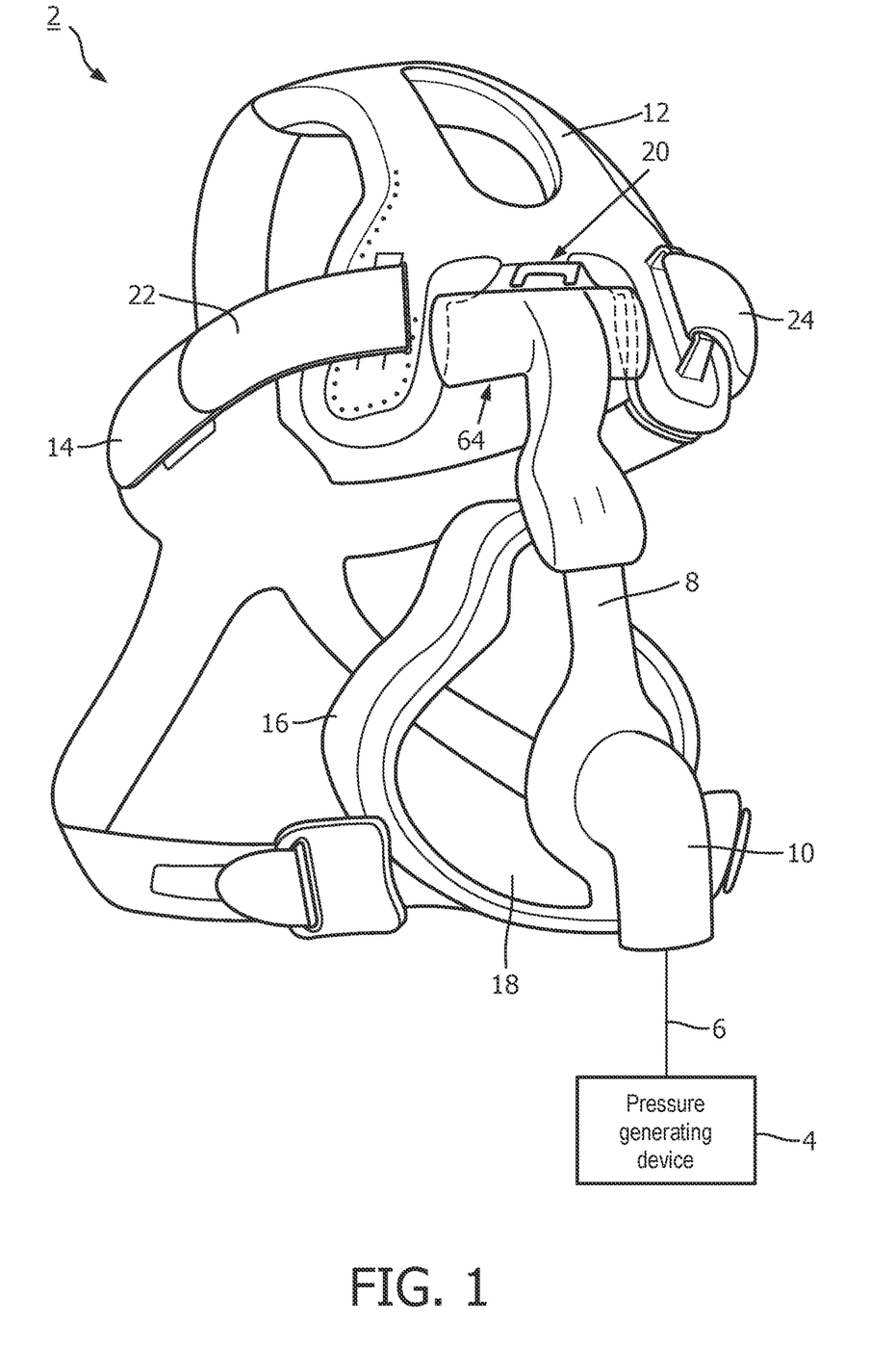
FIG. 1 is one example system (shown partially schematically) for providing a regiment of respiratory therapy to a patient in which one exemplary embodiment of the present invention may be employed.

A system 2 (shown partially schematically) for providing a regiment of respiratory therapy to a patient (not shown) in which one exemplary embodiment of the present invention may be employed is generally shown in FIG. 1. System 2 includes a pressure generating device 4 (shown schematically), a delivery conduit 6 (shown schematically), a patient interface device 8 having a fluid coupling conduit 10, an upper frame 12 and a headgear 14. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pennsylvania), and auto-titration pressure support devices. Delivery conduit 6 is structured to communicate the flow of breathing gas from pressure generating device 4 to patient interface device 8 through fluid coupling conduit 10. In the exemplary embodiment illustrated in FIG. 1, fluid coupling conduit 10 is an elbow connector, however, it is to be appreciated that other suitable couplings may be employed without varying from the scope of the present invention. It is also to be appreciated that conduit 6 may be directly coupled to patient interface device 8 without the use of any intermediary coupling, such as conduit 10.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating device 4 is also referred to as a gas flow generating device, because flow results when a pressure gradient is generated. The present invention contemplates that pressure/flow generating device 4 is any conventional system for delivering a flow of gas to an airway of a patient or for elevating a pressure of gas at an airway of the patient, including the pressure support systems summarized above and non-invasive ventilation systems.

Continuing to refer to FIG. 1, patient interface device 8 includes a cushion 16 coupled to a main frame 18. As commonly known, cushion 16 is generally formed from a soft, pliable material (e.g., without limitation, silicone) and is structured to sealingly engage face of the patient about the mouth and nares of the patient. As also commonly known, main frame 18 is generally formed from a rigid or semi-rigid material (e.g., without limitation, a polycarbonate material) and is structured to generally support cushion 16 in place on the face of a patient. Main frame 18 is pivotally coupled to upper frame 12 at a hinge 20 that provides for patient interface device 8 to be pivoted up and away from, and down and in engagement with the face of a patient while upper frame 12 is secured on the head of the patient via straps 22 and 24 provided as portions of headgear 14. Meanwhile, straps 26 and 28, provided as further portions of headgear 14, may be selectively coupled to, and uncoupled from, patient interface device 8 to secure patient interface 8, and thus cushion 16 thereof, to the face of the patient or allow for removal therefrom (without needing to remove or adjust upper frame 14 relative to the patient).

Although patient interface device 8 is depicted as a nasal/oral mask such as the AF531 Oro-nasal mask manufactured and distributed by Philips Respironics of Murrysville, Pennsylvania, it is to be appreciated that patient interface device 8 is provided for example purposes only and that embodiments of the present invention may be employed with patient interface devices of other designs from any manufacturer that facilitate the delivery of the flow of breathing gas to the airway of the user without varying from the scope of the present invention. It is also to be appreciated that headgear 14 is provided solely for exemplary purposes and that any suitable headgear arrangement may be employed without varying from the scope of the present invention.

Figure 2:
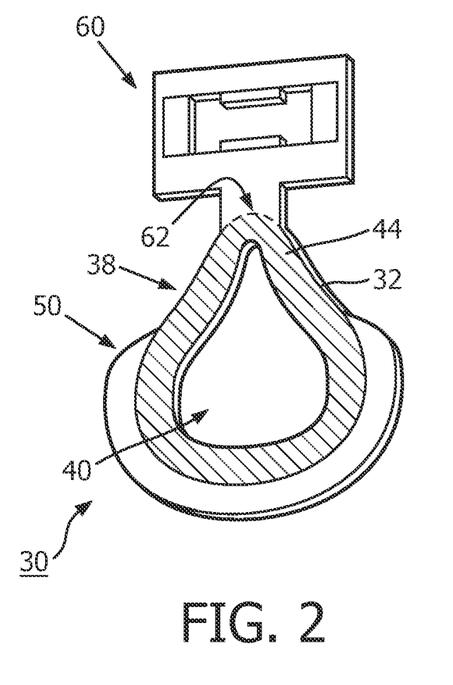
FIG. 2 is an perspective view of a sealing arrangement in accordance with one example embodiment of the present invention.
Figure 3:
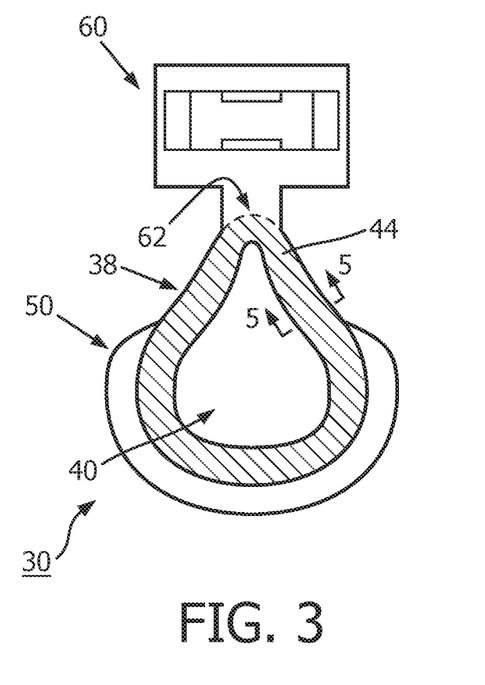
FIG. 3 is an elevation view of a first side of the sealing arrangement of FIG. 2 that is intended to be adhered to a patient interface device.
Figure 4:
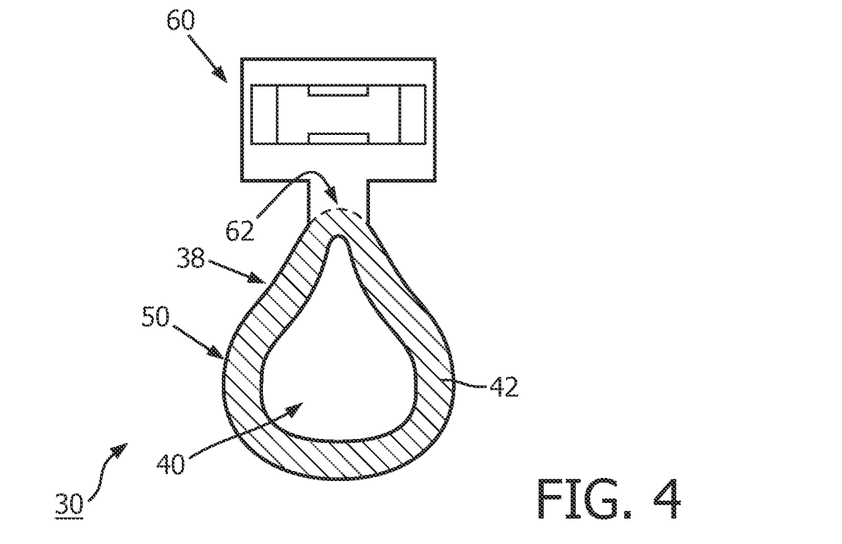
FIG. 4 is an elevation view of a second side, opposite the first side shown in FIG. 3, of the sealing arrangement of FIG. 2 that is intended to be adhered to the face of a patient.
Figure 5:
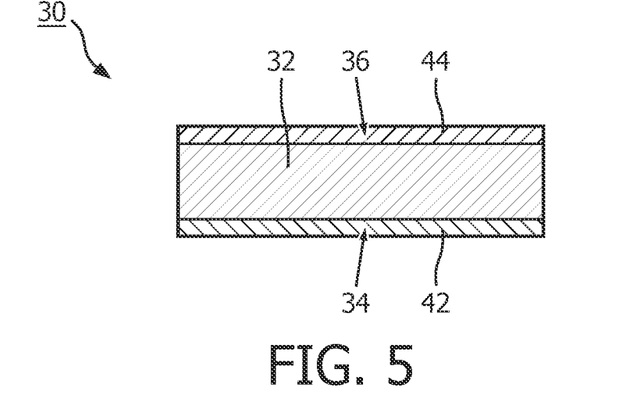
FIG. 5 is a sectional view of a portion of the sealing arrangement of FIG. 2, such as indicated at 5-5 in FIG. 3, showing layers of the sealing arrangement.

Referring now to FIGS. 2-5, a sealing arrangement 30 in accordance with one example embodiment of the present invention for use in forming a generally leak-proof seal between a face of a patient and cushion 16 of patient interface device 8 (for use in delivering a flow of a treatment gas to the patient) is shown. As shown in the sectional view of FIG. 5, sealing arrangement 30 includes a generally planar substrate body 32 having a first side 34 and a second side 36 opposite first side 34. Substrate body 32 may be formed from a foam or other suitably compliant material or materials. As shown in FIGS. 2-4, substrate body 32 includes a main portion 38 having an opening 40 defined therethrough that is sized and configured to encompass the mouth and nose of a patient. In general, main portion 38 is generally sized like a 2D projection of the patient contacting portion of cushion 16. In one example embodiment of the present invention, opening 40 is sized so as to be slightly larger than the corresponding patient opening of the cushion to which it is adhered.

In order to form the seal between the face of the patient and cushion 16 of patient interface device 8, sealing arrangement 30 further includes a first adhesive layer 42 (shown as hatching in FIG. 4) disposed on first side 34 of substrate body 32 and a second adhesive layer 44 (shown as hatching in FIGS. 2 and 3) disposed on second side 36 of substrate body 32. First adhesive layer 42 is sized and configured (i.e., of a suitable arrangement and composition) to adhere to the skin of the patient adjacent the nose and mouth of the patient with a first adherence force. Second adhesive layer 44 is sized and configured (i.e., of a suitable arrangement and composition) to adhere to cushion 16 of patient interface device 8 with a second adherence force less than the first adherence force. Such difference between the first and second adherence forces provides for cushion 16 to be un-adhered (i.e., separated) from sealing arrangement 30 while sealing arrangement 30 is adhered to the face of the patient.

Continuing to refer to FIGS. 2-4, in order to increase the strength of the adherence of sealing arrangement 30 to the face of the patient and/or to assist in un-adherence/removal of cushion 16 from sealing arrangement 30 while sealing arrangement 30 is adhered to the patient, substrate body 32 may further include an extension tab 50 that extends from main portion 38. As shown in FIG. 4, first adhesive layer 42 extends onto extension tab 50, hence extension tab 50 includes a portion of first adhesive layer 42 thereon. As shown in FIGS. 2 and 3, second adhesive layer 44 does not extend onto extension tab 50, hence extension tab 50 does not include a portion of second adhesive layer 44. Alternatively, second adhesive layer 44 may extend onto extension tab 50 but be covered by a layer of a release or other suitable material that covers the portion of second adhesive layer 44 on extension tab 50. In either case, the outward facing side of extension tab 50 (i.e., the continuation of second side 36 of substrate body 32) is left unsticky, so as to provide a gripping/holding surface for assisting in maintaining adherence of sealing arrangement to the face of the patient while cushion 16 is un-adhered/removed therefrom, as discussed further below.

In the one example embodiment shown in FIGS. 2-4, extension tab 50 is sized and configured to extend downward along a first side of the mouth of the patient, across below the mouth of the patient, and upward along a second side of the mouth of the patient opposite the first side of the mouth when the sealing arrangement is positioned on the face of the patient with opening 40 encompassing the mouth and nose of the patient.

In order to assist in properly initially aligning sealing arrangement 30 with patient interface 8 and cushion 16 thereof, substrate body 32 of sealing arrangement 30 may further comprise an alignment portion 60 that extends from main portion 38. Alignment portion 60 may be delineated from main portion 38 by a separation feature 62 (shown in dashed line in FIGS. 2-4) that generally provides for a one-time uncoupling of alignment portion 60 from main portion 38. In one example embodiment of the present invention separation feature 62 includes a locally thinned region (e.g., a groove or score) extending between alignment portion 60 and main portion 38 that has been formed in substrate body 32. In one example embodiment of the present invention separation feature 62 includes a plurality of separations defined through substrate body 32. In one example embodiment such as shown in FIGS. 2-4, alignment portion 60 is sized and configured to engage a forehead support of a patient interface device, such as forehead support 64 of patient interface device 8 of FIG. 1.

Figure 6A:
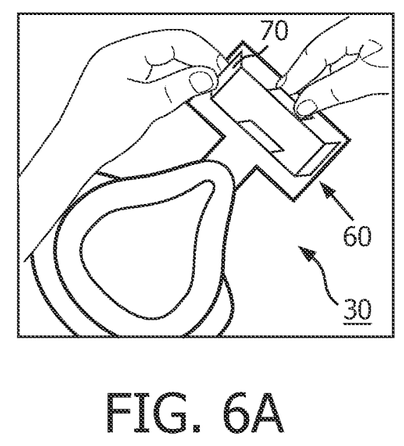
FIGS. 6A-6T illustrate steps of a method in accordance with one example embodiment of the present invention of using the sealing arrangement of FIG. 2 to selectively adhere and seal the patient interface device of FIG. 1 to the face of a patient.
Figure 6B:
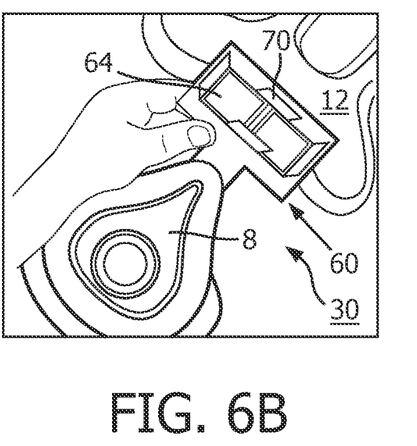

Having thus described one example embodiment of sealing arrangement 30 in accordance with the present invention, a method of using sealing arrangement 30 to selectively seal cushion 16 of patient interface 8 of FIG. 1 to a patient will now be described in conjunction with FIGS. 6A-6T. Referring first to FIGS. 6A and 6B, sealing arrangement 30 is prepared and test fit to patient interface device 8. In such example, such preparation includes bending a number of fitment tabs 70 (only one is numbered) provided with alignment portion 60 in order to engage alignment portion 60 with a portion (e.g., without limitation, a rectangular forehead pad) of forehead support 64 of patient interface device 8.

Figure 6C:
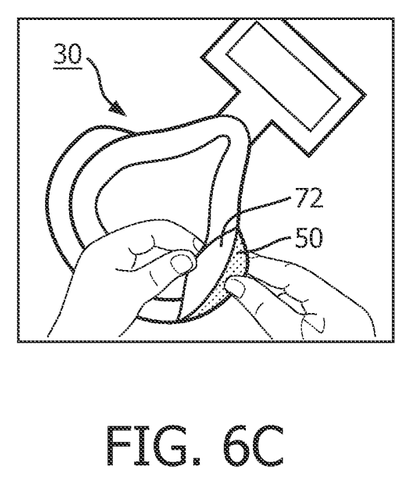
Figure 6D:
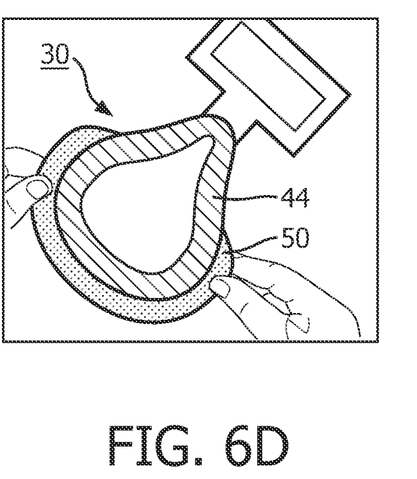
Figure 6E:
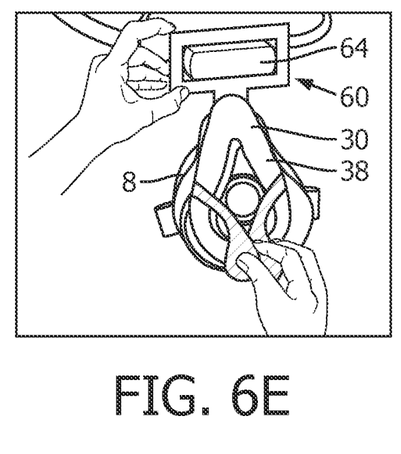
Figure 6F:
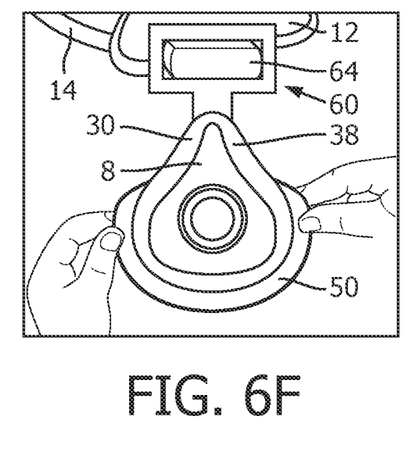
Figure 6G:
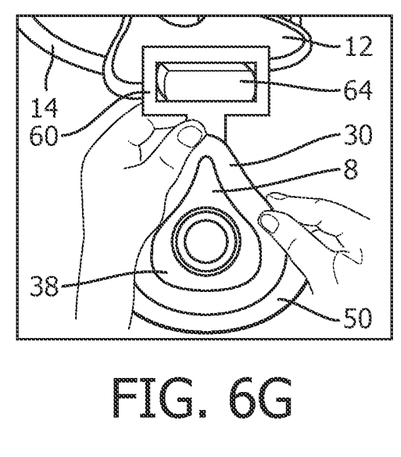
Figure 6H:
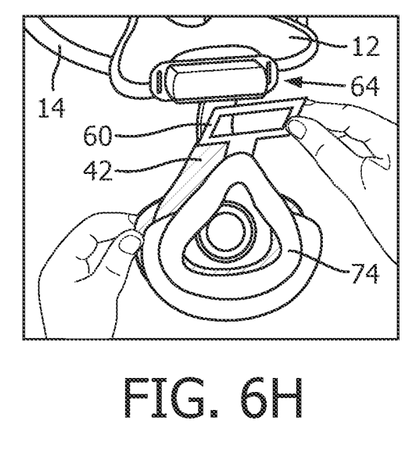
Figure 6I:
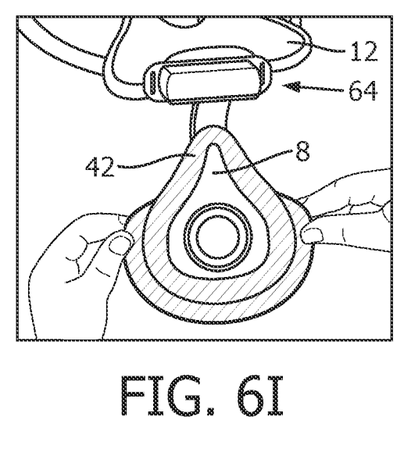

Moving on to FIGS. 6C and 6D, after test fitting sealing arrangement 30 to patient interface device 8, sealing arrangement 30 is removed therefrom and a release layer 72 covering at least second adhesive layer 44 is removed from sealing arrangement 30. In the example shown in FIG. 6C, release layer 72 not only covers second adhesive layer 44 but additionally covers at least a portion of extension tab 50. Hence, such arrangement provides for an easy peel tab on release layer 72 since the portion thereof overlying extension tab 50 is not adhered to extension tab 50 by any adhesive material. Now that second adhesive layer 44 has been exposed, sealing arrangement 30 is aligned with patient interface device 8 by aligning alignment portion 60 with forehead support 64 and slowly bringing second adhesive layer 44 into contact with cushion 16 of patient interface device 8, such as generally shown in FIGS. 6E and 6F. Next, as shown in FIG. 6G, main portion 38 of sealing arrangement 30, and particularly the outer perimeter thereof, is pressed against cushion 16 to ensure good adherence between sealing arrangement 30 and cushion 16. After main portion 38 of sealing arrangement 30 has been sufficiently adhered to cushion 16, alignment portion 60 of sealing arrangement 30 is disengaged from patient interface device 8 and uncoupled from main portion 38. In the example shown in FIG. 6H, a second release layer 74 covering first adhesive layer 42 is coupled to alignment portion 60 and thus is removed from sealing arrangement 30 along with alignment portion 60, thus exposing first adhesive layer 42 of sealing arrangement 30. It is to be appreciated that such arrangement of alignment portion 60 and second release layer 74 generally serves to provide an easy pull tab, i.e., alignment portion 60, for removing second release layer 74.

Figure 6J:
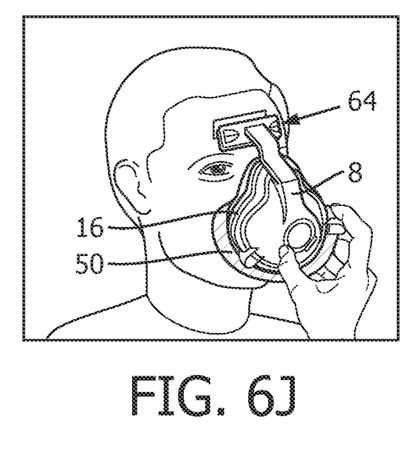
Figure 6K:
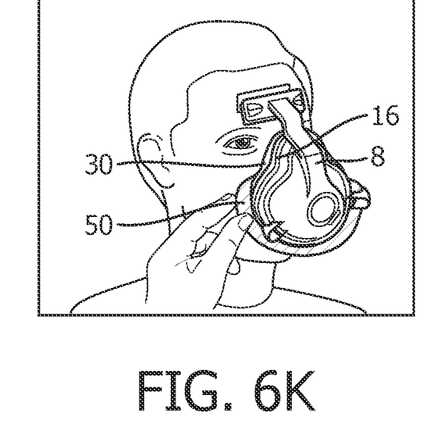
Figure 6L:
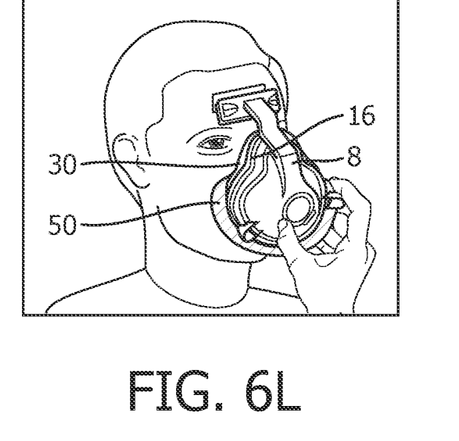
Figure 6M:
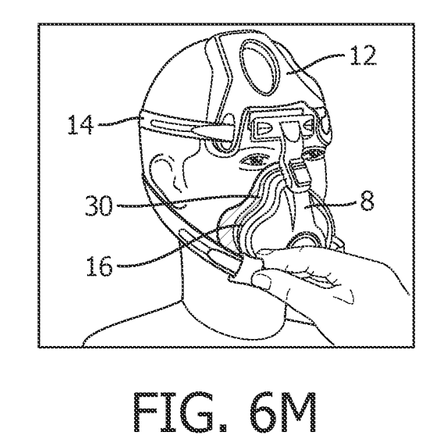
Figure 6N:
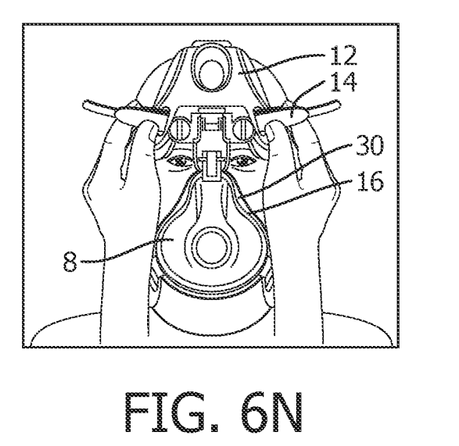

Moving on now to FIGS. 6J-6L, after first adhesive layer has been exposed, patient interface 8 and sealing arrangement 30 adhered thereto are aligned and adhered to the face of the patient (not numbered). Such adherence may be accomplished by grasping and pressing patient interface 8 toward the face of the patient. To firm up the seal between sealing arrangement 30 and the face of the patient, extension tab 50 is also pressed along the length thereof to ensure adhesion thereof near the mouth and chin of the patient. After sealing arrangement 30 and patient interface device 8 have been adhered to the face of the patient, upper frame 12 is coupled to main frame 18 of patient interface device 8 and the assembly is further secured to the head of the patient via headgear 14, such as generally shown in FIGS. 6M and 6N. Upon completion of such steps, patient interface device 8 is sealingly engaged to the face of the patient via sealing arrangement 30 and thus ready for coupling to, and receiving a flow of a treatment gas from, pressure generating device 4.

Figure 6O:
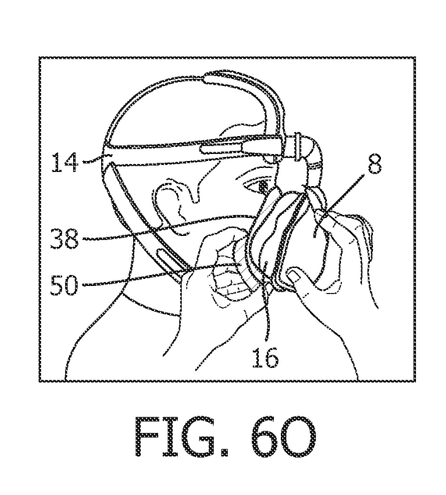
Figure 6P:
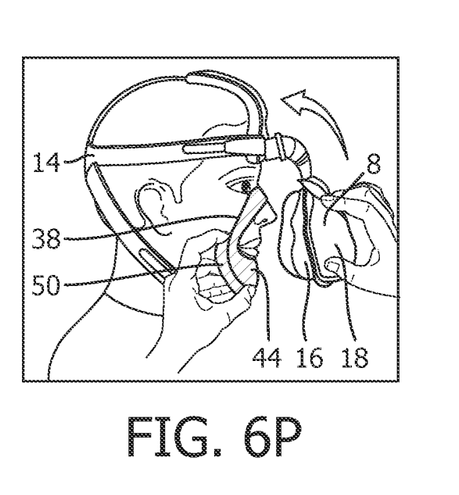
Figure 6Q:
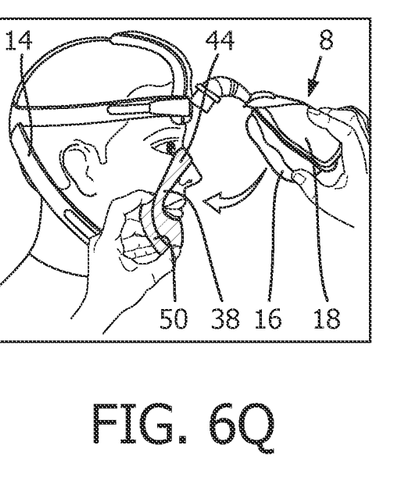
Figure 6R:
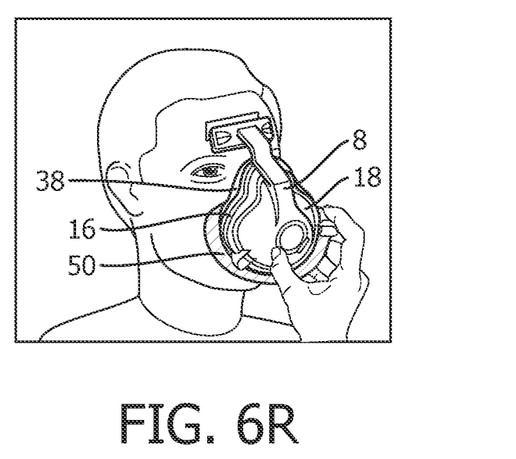
Figure 6S:
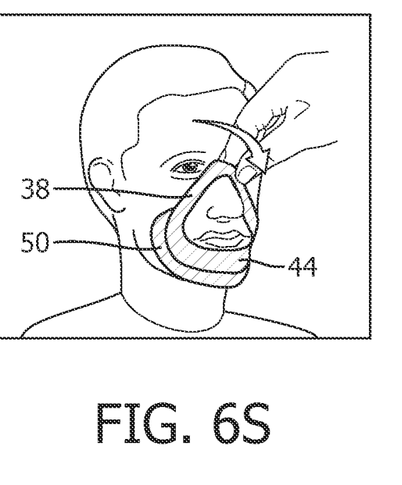
Figure 6T:
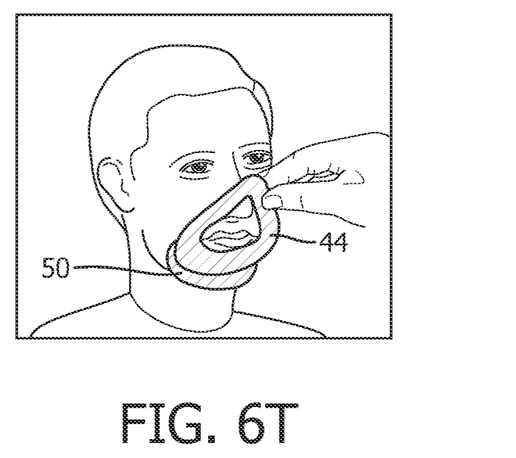

If/when a need arises for patient interface device 8 to be temporarily removed from the face of the patient, sealing arrangement 30 may be generally held in place on the face of the patient by pressing against extension tab 50 as shown in FIG. 6O. Next, as shown in FIG. 6P, patient interface device 8 is separated/un-adhered from second adhesive layer 44 by grasping main frame 18 thereof and pulling away from the face of the patient and sealing arrangement 30. As shown in FIGS. 6Q and 6R, patient interface device 8, and more particularly cushion 16 thereof, may be re-adhered/sealed to the face of the patient simply by moving cushion 16 back into contact with second adhesive layer 44 and pressing patient interface device 8 into engagement therewith to ensure adequate adherence/seal. The remaining portions of sealing arrangement 30, i.e., main portion 38 and extension tab 50 may be removed/un-adhered from the face of the patient simply by grasping and peeling away from the face of the patient, such as shown in FIGS. 6S and 6T. As shown in such FIGS., removal of such remaining portions may be accomplished by starting at the top of the nose and peeling generally downward, in-line with the skin of the patient.

From the foregoing description it is thus to be appreciated that embodiments of the present invention provide arrangements that improve the seal between a patient interface device and the face of a patient. It is also to be appreciated that such arrangements reduce the potential for Medical Adhesive Related Skin Injury (MARSI) to occur by reducing the need to adhere/remove an adhesive from the skin of the patient multiple times in a given period by providing for the adhesive to remain on the patient while the patient interface device is removed. In a normal use case (i.e., a conventional NIV usage in a non COVID-19 situation), an NIV mask can be removed an average of 14 times a day. With the COVID-19 pandemic use case, the conventional masks can be expected to be removed around 4 times a day (less to prevent viral spread). Adhesive removal in a repeated area even 4 times a day, puts patients at a high risk for MARSI. Sealing arrangement in accordance with example embodiments of the present invention overcome this issue by remaining on the face of the patient while allowing the mask/patient interface device to be removed and reapplied a number of times (at minimum 7).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A sealing arrangement for use in forming a seal between a face of a patient and a patient interface device for use in delivering a flow of a treatment gas to the patient, the sealing arrangement comprising:
    a generally planar substrate body having a first side and a second side opposite the first side, the substrate body comprising a main portion having an opening defined therethrough, the opening being sized and configured to encompass the mouth and nose of the patient;
    a first adhesive layer disposed on the first side of the substrate body; and
    a second adhesive layer disposed on the second side of the substrate body,
    wherein the first adhesive layer is sized and configured to adhere to the skin of the patient adjacent the nose and mouth of the patient with a first adherence force,
    wherein the second adhesive layer is sized and configured to adhere to a cushion of the patient interface device with a second adherence force less than the first adherence force,
    wherein the substrate body further comprises an extension tab extending from the main portion and including a portion of the first adhesive layer thereon configured to adhere to the skin of the patient, and
    wherein the extension tab is sized and configured to extend downward along a first side of the mouth of the patient, across below the mouth of the patient, and upward along a second side of the mouth of the patient opposite the first side of the mouth when the sealing arrangement is positioned on the face of the patient with the opening encompassing the mouth and nose of the patient.

2. The sealing arrangement of claim 1, wherein the substrate body further comprises an alignment portion extending from the main portion.

3. The sealing arrangement of claim 2, wherein the alignment portion is delineated from the main portion by a separation feature.

4. The sealing arrangement of claim 3, wherein the separation feature comprises a locally thinned region extending between the alignment portion and the main portion in the substrate body.

5. The sealing arrangement of claim 3, wherein the separation feature comprises a plurality of separations defined through the substrate body.

6. The sealing arrangement of clam 4, wherein the alignment portion is sized and configured to engage a forehead support of the patient interface device.

7. The sealing arrangement of claim 1, wherein the substrate body further comprises an alignment portion extending from the main portion.

8. The sealing arrangement of claim 7, wherein the alignment portion is delineated from the main portion by a separation feature.

9. The sealing arrangement of claim 8, wherein the separation feature comprises one of a locally thinned region extending between the alignment portion and the main portion in the substrate body, or a plurality of separations defined through the substrate body.

10. The sealing arrangement of clam 9, wherein the alignment portion is sized and configured to engage a forehead support of the patient interface device.

11. An arrangement for use in delivering a flow of a treatment gas to a patient, the arrangement comprising:
a patient interface device having a cushion structured to sealingly engage about the mouth and nose of the patient; and
a sealing arrangement comprising:
a generally planar substrate body having a first side and a second side opposite the first side, the substrate body comprising a main portion having an opening defined therethrough, the opening being sized and configured to encompass the mouth and nose of the patient;
a first adhesive layer disposed on the first side of the substrate body; and
a second adhesive layer disposed on the second side of the substrate body,
wherein the first adhesive layer is sized and configured to adhere to the skin of the patient adjacent the nose and mouth of the patient with a first adherence force,
wherein the second adhesive layer is adhered to the cushion of the patient interface device with a second adherence force less than the first adherence force,
wherein the substrate body further comprises an extension tab extending from the main portion and including a portion of the first adhesive layer thereon configured to adhere to the skin of the patient, and
wherein the extension tab is sized and configured to extend downward along a first side of the mouth of the patient, across below the mouth of the patient, and upward along a second side of the mouth of the patient opposite the first side of the mouth when the sealing arrangement is positioned on the face of the patient with the opening encompassing the mouth and nose of the patient.

12. The arrangement of claim 11, wherein the opening defined through the main portion of the substrate body is larger than a corresponding patient opening of the cushion.

13. A method of selectively sealing a cushion of a patient interface device to the face of a patient using a sealing arrangement, the method comprising:
(a) providing the sealing arrangement comprising:
(1) a generally planar substrate body having a first side and a second side opposite the first side, the substrate body comprising a main portion having an opening defined therethrough, the opening being sized and configured to encompass the mouth and nose of the patient
(2) a first adhesive layer disposed on the first side of the substrate body; and
(3) a second adhesive layer disposed on the second side of the substrate body, wherein the first adhesive layer is sized and configured to adhere to the skin of the patient adjacent the nose and mouth of the patient with a first adherence force, wherein the second adhesive layer is sized and configured to adhere to a cushion of the patient interface device with a second adherence force less than the first adherence force, wherein the substrate body further comprises an extension tab extending from the main portion and including a portion of the first adhesive layer thereon configured to adhere to the skin of the patient, and wherein the extension tab is sized and configured to extend downward along a first side of the mouth of the patient, across below the mouth of the patient, and upward along a second side of the mouth of the patient opposite the first side of the mouth when the sealing arrangement is positioned on the face of the patient with the opening encompassing the mouth and nose of the patient
coupling the substrate body of the sealing arrangement to the cushion with the second adhesive layer;
coupling the substrate body and the cushion coupled to the substrate body to the face of the patient with the first adhesive layer;
uncoupling the cushion from the substrate body while leaving the substrate body coupled to the face of the patient by separating the cushion from the second adhesive layer; and
recoupling the cushion to the substrate body while the substrate body is coupled to the face of the patient via the first adhesive layer by re-adhering the second adhesive layer to the cushion.

* * * * *